(12) United States Patent
Thompson et al.

(10) Patent No.: US 8,372,441 B2
(45) Date of Patent: Feb. 12, 2013

(54) MATERIALS AND METHODS FOR PREPARATION OF ALKALINE EARTH FERRATES FROM ALKALINE EARTH OXIDES, PEROXIDES, AND NITRATES

(75) Inventors: John Alfred Thompson, Nassau (BS); John Hen, Bradenton, FL (US)

(73) Assignee: Biolife, LLC, Sarasota, FL (US)

( * ) Notice: Subject to any disclaimer, the term of this patent is extended or adjusted under 35 U.S.C. 154(b) by 52 days.

(21) Appl. No.: 12/627,900

(22) Filed: Nov. 30, 2009

(65) Prior Publication Data

US 2010/0151049 A1    Jun. 17, 2010

Related U.S. Application Data (63) Continuation-in-part of application No. PCT/US2008/065357, filed on May 30, 2008.

(60) Provisional application No. 60/932,610, filed on May 31, 2007.

(51) Int. Cl.
| | |
|---|---|
| A61K 33/26 | (2006.01) |
| A61K 9/00 | (2006.01) |
| C01G 49/02 | (2006.01) |
| C01G 29/00 | (2006.01) |
| C01F 11/02 | (2006.01) |
| A61P 7/04 | (2006.01) |

(52) U.S. Cl. ............... 424/646; 424/400; 423/594.2; 423/594.7; 423/594.16

(58) Field of Classification Search .................. None
See application file for complete search history.

(56) References Cited

U.S. PATENT DOCUMENTS

| | | | |
|---|---|---|---|
| 2,366,007 A | 12/1944 | D'Alelio | |
| 3,463,320 A | 8/1969 | Patterson | |
| 3,669,103 A | 6/1972 | Harper et al. | |
| 3,670,731 A | 6/1972 | Harmon | |
| 4,291,980 A | 9/1981 | Patterson | |
| 4,545,974 A | 10/1985 | Thompson | |
| 4,551,326 A * | 11/1985 | Thompson | 423/594.2 |
| 4,654,039 A | 3/1987 | Brandt et al. | |
| 5,461,085 A | 10/1995 | Nagatomo et al. | |
| 5,525,703 A | 6/1996 | Kalota | |
| 5,612,384 A | 3/1997 | Ross et al. | |
| 6,187,347 B1 | 2/2001 | Patterson et al. | |
| 6,238,691 B1 | 5/2001 | Huang | |
| 6,271,278 B1 | 8/2001 | Park et al. | |
| 6,326,410 B1 | 12/2001 | Cheong | |
| 6,399,092 B1 | 6/2002 | Hobson et al. | |
| 6,500,539 B1 | 12/2002 | Chen et al. | |
| 6,521,265 B1 | 2/2003 | Patterson | |
| 6,787,682 B2 | 9/2004 | Gilman | |
| 6,861,067 B2 | 3/2005 | McGhee et al. | |
| 6,936,746 B2 | 8/2005 | Effing et al. | |
| 6,960,617 B2 | 11/2005 | Omidian et al. | |
| 7,005,556 B1 | 2/2006 | Becker et al. | |
| 7,030,288 B2 | 4/2006 | Liedtke et al. | |
| 7,056,957 B2 | 6/2006 | Omidian et al. | |
| 7,070,584 B2 | 7/2006 | Johnson et al. | |
| 7,112,714 B2 | 9/2006 | Leber | |
| 7,252,837 B2 | 8/2007 | Guo et al. | |
| 2001/0038831 A1 | 11/2001 | Park et al. | |
| 2002/0141964 A1 | 10/2002 | Patterson et al. | |
| 2003/0008007 A1 | 1/2003 | Gutierrez-Rocca et al. | |
| 2003/0232895 A1 | 12/2003 | Omidian et al. | |
| 2004/0224021 A1 | 11/2004 | Omidian et al. | |
| 2007/0269499 A1 | 11/2007 | Hen et al. | |

FOREIGN PATENT DOCUMENTS

| | | | |
|---|---|---|---|
| EP | 0312952 A2 | | 4/1989 |
| EP | 0441507 A1 | | 8/1991 |
| WO | WO 99/29628 | * | 6/1999 |
| WO | WO 01/82896 A1 | | 11/2001 |

OTHER PUBLICATIONS

Dann et al. The Synthesis and Structure of Sr2FeO4. Journal of Solid State Chemistry 92, 237-240 (1991).*

* cited by examiner

*Primary Examiner* — Scott Long
*Assistant Examiner* — Sarah Alawadi
(74) *Attorney, Agent, or Firm* — Saliwanchik, Lloyd & Eisenschenk; Doran R. Pace (57) ABSTRACT

The subject invention concerns methods for preparing alkaline earth ferrates and the preparation of hemostatic compositions from alkaline earth ferrates. In one embodiment, the alkaline earth ferrate is strontium ferrate. In one embodiment, methods of the invention comprise heat treating mixtures of alkaline earth oxides and/or peroxides with iron oxides, such as hematite or magnetite. The subject invention also concerns hemostatic compositions produced using metallic oxides that are reacted with alkaline earth oxides and/or peroxides and the methods used to produce the hemostatic compositions.

19 Claims, 8 Drawing Sheets

MATERIALS AND METHODS FOR PREPARATION OF ALKALINE EARTH FERRATES FROM ALKALINE EARTH OXIDES, PEROXIDES, AND NITRATES

CROSS-REFERENCE TO RELATED APPLICATIONS

This application is a continuation-in-part of International Application No. PCT/US2008/065357, filed. May 30, 2008, which claims the benefit of U.S. Provisional Application Ser. No. 60/932,610, filed May 31, 2007, each of which is hereby incorporated by reference herein in its entirety, including any and all text, examples, figures, tables, nucleic acid sequences, amino acid sequences, and drawings.

BACKGROUND OF THE INVENTION

Alkaline earth metals include beryllium (Be), magnesium (Mg), calcium (Ca), strontium (Sr), barium (Ba), and radium (Ra). All alkaline earth oxides and peroxides will clot blood to some degree. The clot, however, is of generally poor quality. Beryllium and barium exhibit some toxicity to living systems, and therefore should be used on humans and other mammals with caution. Barium could be considered for life saving hemostasis where it is only used once, as it is not as toxic as beryllium. The alkaline earth oxides and peroxides of choice would be magnesium, calcium and strontium. However, the oxides of these three metals show relatively poor hemostasis as they tend to float on blood, forming a thin clot between the interface of the blood and oxide powder. This inhibits further absorbance of blood into the oxide powder and the clot is very weak, causing it to be ruptured by blood pressure. They also generate heat when put in contact with water. Strontium oxide tends to combine with blood better than MgO or CaO, producing some hemostasis.

The peroxides of Mg, Ca and Sr are candidates for use in hemostasis. Zinc peroxide ($ZnO_2$), although not an alkaline earth oxide, has some hemostatic activity. All four of these peroxides (as dry powders) tend to be absorbed and interact with mammalian blood producing a clot suitable for hemostasis in humans.

Classically, barium ferrate ($BaFeO_4$) and strontium ferrate ($SrFeO_4$) are produced in aqueous solution by precipitation of a mixture of an alkali metal ferrate ($Na_2FeO_4$ or $K_2FeO_4$) and a soluble salt of barium (Ba) or strontium (Sr), e.g. $BaCl_2$, $SrCl_2$. These alkaline earth ferrates are practically insoluble in water, and may be removed by filtration or centrifugation. The product is then washed repeatedly with water in order to remove the unwanted cations (e.g. $Na^+$, $K^+$), and the carrier anions of the Ba or Sr (e.g. $Cl^-$). These alkaline earth ferrates, with Fe in the +4 and/or +6 oxidation state, have value as hemostatic agents, as catalysts, and as electron acceptors in dry cell primary and secondary batteries, and any reaction where a strong oxidant is utilized.

BRIEF SUMMARY OF THE INVENTION

The subject invention concerns methods for preparing alkaline earth ferrates. In one embodiment, the alkaline earth ferrate is strontium ferrate. In one embodiment, methods of the invention comprise heat treating mixtures of alkaline earth oxides and/or peroxides with iron oxides, such as hematite or magnetite. In another embodiment, alkaline earth ferrates are produced by heating mixtures of alkaline earth nitrates and iron oxides. The subject invention also concerns hemostatic and wound healing compositions produced using manganese oxides or metallic oxides that are reacted with alkaline earth oxides and/or peroxides and the methods used to produce the hemostatic and wound healing compositions.

DETAILED DISCLOSURE OF THE INVENTION

The subject invention concerns methods and materials for synthesis of alkaline earth ferrates of the formula $M_2FeO_4$ (Fe in the +4 oxidation state) (wherein M is the alkaline earth metal), such as $Sr_2FeO_4$. Methods of the invention are advantageous because they greatly simplify the production of alkaline earth ferrates such as $Sr_2FeO_4$. In one embodiment, a method of the invention comprises heat treating mixtures of alkaline earth oxides and/or peroxides with iron oxides. The molar ratio of the metal in alkaline earth oxide/peroxide to Fe in the mixture can range from about 5:1 to about 1:5. In one embodiment, the molar ratio of the metal in the alkaline earth oxide/peroxide (e.g., Sr) to Fe is about 3:1, or about 2:1, or about 1:1. For strontium ferrate production, the molar ratio of Sr to Fe can be from 0.5:1 to 5.0:1. A preferred range of molar ratio of Sr to Fe is from 1:1 to 3.5:1. In one embodiment, the reactants are heated together at a temperature greater than about 400° C. for a period of time ranging from several minutes to several hours. In one embodiment, the reactants are heated together at a temperature greater than about 400° C. for about 15 hours. In a further embodiment, the reaction takes place between 400° C. and 700° C. for between about 1 hour to 7 hours or more. In one embodiment, the reactants are heated at about 500° C. for about 3 hours. In a still further embodiment, the reactants are heated at about 600° C. for about 30 minutes. In yet a further embodiment, the reactants are heated at about 700° C. for between about 15 minutes and about 30 minutes.

In an exemplified embodiment, a method of the invention for producing strontium ferrate involves an intimate mixture of about 1.3 grams $Fe_2O_3$ and about 2.0 grams of strontium peroxide ($SrO_2$), with a molar ratio of about 1:1, the mixture is heated to about 500° C. for about 3 hours in a stainless steel or ceramic vessel. The strontium ferrate ($Sr_2FeO_4$) yield is greater than 53% and the impurities are $Fe_2O_3$, strontium carbonate ($SrCO_3$) and strontium hydroxide ($Sr(OH)_2$). In another embodiment, an excess of strontium peroxide or strontium oxide (in relation to the Fe; i.e., molar Sr>Fe) is used in the mixture. The mixture of reactants wherein strontium is in molar excess compared to iron produces a composition with excellent hemostatic properties, including excellent clot strength and adhesion and rapid clotting time.

In another embodiment, magnetite ($Fe_3O_4$) may be used in place of $Fe_2O_3$ as an iron oxide source in the methods of the present invention. In one embodiment, the Sr:Fe molar ratio in the reactant mixture is about 1:1. For reactant mixture of about 1:1 of magnetite and strontium peroxide, the yield of strontium ferrate ($Sr_2FeO_4$) is above 48%.

The subject invention also concerns hemostatic compositions produced using metallic oxides reacted with an alkaline earth oxide and/or peroxide, such as strontium. These compositions can be produced by heating mixtures of metallic oxides and $SrO_2$. In one embodiment, a metallic oxide is mixed with an alkaline earth oxide and/or peroxide and the mixture heated for several hours. In one embodiment, the reactants are heated together at a temperature greater than about 400° C. for a period of time ranging from several minutes to several hours. In one embodiment, the reactants are heated together at a temperature greater than about 400° C. for about 15 hours. In a further embodiment, the reaction takes place between 400° C. and 700° C., for between about 1 hour to 7 hours or more. In one embodiment, the reactants are heated at about 500° C. for about 3 hours. In a still further embodiment, the reactants are heated at about 600° C. for about 30 minutes. In yet a further embodiment, the reactants are heated at about 700° C. for between about 15 minutes and about 30 minutes. In another embodiment, a metallic oxide is mixed with an alkaline earth oxide and/or peroxide and about 5% to 20% by weight carbon powder, or about 8% to 15% by weight carbon powder, or about 10% by weight carbon powder (in relation to the amount of the alkaline earth oxide and/or peroxide) is added to the mixture. The mixture is ignited with a flame or other heat source. The list of oxides that can be used includes, for example:

Magnesium oxide (MgO)
Aluminum oxide ($Al_2O_3$)
Titanium oxide ($TiO_2$)
Silicon oxide ($SiO_2$)
Cobalt oxide ($CO_3O_4$)
Copper oxide (CuO)
Zinc oxide (ZnO)
Zinc peroxide ($ZnO_2$)
Silver oxide ($Ag_2O$)
Bismuth oxide ($Bi_2O_3$)

These oxides were chosen for their relatively low toxicities. Molybdenum oxide ($MoO_3$, natural molybdite), and tungsten oxide ($WO_3$, natural wolframite), may also have value as hemostats and wound healing agents (or Molybite and tungsten oxides in lower oxidation states).

Some examples of hemostatic compositions produced using metallic oxides are described in Examples 7 and 8 herein.

On testing as hemostats, Al, Mg and Si are very poor blood clotters. Titanium oxide is a (surprisingly) fair clotter. Cobalt (+2,+3) oxide makes an excellent hemostat when 0.5 grams $CO_3O_4$ is mixed with 1.0 gram strontium peroxide and heated at 500° C. for 2 hours. Copper oxide yields a poor clotter, as it tends to react with the blood to form an interface barrier and not be absorbed. Zinc oxide performs about the same as copper oxide. Zinc peroxide (1.0 grams) mixed with strontium peroxide (1.0 grams) makes a surprisingly good clotter when heated to 500° C. for one hour. Only cobalt, silver and bismuth oxides approach the clotting efficiency of the Fe/Sr and Mn/Sr hemostat systems described.

The metallic oxides which combine with alkaline earth peroxides to form superior hemostats are generally those which can be oxidized to a higher state (with the exceptions of the $ZnO_2/SrO_2$ and $CO_3O_4/SrO_2$ reactions, although it is highly likely that cobalt, like iron, can be oxidized beyond +3). Indeed, the existence of tetravalent cobalt is described as "resonance between the trivalent and the tetravalent cobalt atoms, and this must be favored by the presence of the peroxide group" (Sidgwick, 1950). The compounds formed as products are very complex in these high temperature reactions. Most of the information available concerns the ferrates and (per)manganates, but even that is very sparse when dealing with thermal fusion reactions.

A temperature of about 500° C. can be used in the methods of the present invention. The decomposition temperature of strontium peroxide is 480° C. and it is here that the solid state reactions occur (Vol'nov, 1966). This temperature is reported as 215° C. in the CRC Handbook of Chemistry and Physics, although the 480° C. figure seems more realistic.

Testing of the reaction products produced by the methods of the present invention is performed on fresh human blood or EDTA preserved porcine blood. In one embodiment, three to four milliliters of blood is placed on a smooth plastic surface and the product applied to the blood drop, with the results observed over the next few minutes.

All of the hemostatic compounds and compositions produced by the methods described herein may be mixed with various hydrophilic resins, polymers and hydrogels in order to extend their blood clotting capabilities, such as those described in, for example, U.S. Pat. Nos. 6,521,265; 6,187,347; and 6,521,265 and published applications US-2002-0141964 and US-2007-0269499. For example, if about 9 parts (by weight) of the product of Example 2 (Sr/Fe system) is mixed with about 1 part powdered sodium salt of crosslinked polyacrylate, the result is a clot which is considerably more flexible than the product of Example 2 alone when applied to blood.

Compositions of the invention comprising an alkaline earth ferrate of the invention can also comprise one or more cross-linked ionic hydrophilic polymers. Polymers contemplated within the scope of the invention include, but are not limited to, carboxyvinyl polymer such as polymethacrylic acid, and, biodegradable crosslinked sodium carboxymethylcellulose or similar derivatives, biodegradable crosslinked starches (for example, LYSORB, Archer Daniels Midland Corporation, Decatur, Ill.), guar gums, Arabic gums, karaya and other natural gums. Polyacrylic acid polymer comprises the structure:

The salt form of a polyacrylic acid polymer comprises the structure (where M is a metal ion or other suitable ion):

The salt form of polymers of the invention, such as polyacrylic acid, can be prepared from any suitable metal ion including, but not limited to, sodium, lithium, potassium, and calcium. Ammonium and triethanolamine salts of polyacrylate are also contemplated within the scope of the invention. In one embodiment, a polyacrylic acid is provided as sodium polyacrylate. In a specific embodiment, the sodium polyacrylic acid is that form described for CAS registration number 9003-04-7.

In one embodiment, cross-linked ionic polymers used in a composition of the invention are super absorbing polymers (e.g., U.S. Pat. Nos. 5,525,703; 5,612,384; 5,461,085; 4,654,039; 3,670,731; 3,669,103; EP 0312952 and EP 0441507) or ionic hydrogels that can absorb and retain close to 20 times its own weight in water. Super absorbing polymers contemplated for use with the invention include, but are not limited to, polymers or copolymers of acrylic acid or methacrylic acid, or graft copolymers of acrylic acid and starch. This is to be differentiated by polyurethane hydrogels that can absorb but not retain (easily pushed out) the same amount of water. A hydrogel is a three-dimensional network of hydrophilic polymer chains that are crosslinked. The hydrogel is characterized by its extractables. A polyacrylic acid polymer of the invention preferably has percentage extractables in the range of from about 5% to about 30%. Extractables are the soluble components in the gel which include lightly crosslinked polymers. The linear or lightly crosslinked extractables can have a molecular weight in the range of 200,000 to 2 million. Particles of polyacrylic acid polymer can range in size from about 25 to about 1,000 microns. In an exemplified embodiment, a composition of the invention comprises sodium polyacrylate provided in a dry powdered form. The polyacrylate composition can be applied directly to a wound or treatment site, or it can be incorporated into a wound or surgical dressing, such as a bandage. The clot or scab formed at a wound or treatment site treated with the present invention is extremely elastic and exhibits considerable tensile strength when stretched to the breaking point.

Polymers of the invention also include superporous hydrogels (e.g., U.S. Pat. Nos. 6,271,278; 6,960,617; 7,056,957; and published U.S. application Nos. 20030008007; 20010038831; 200302332895; and 2004022402). Superporous hydrogels (for example, AQUAGEL, Akina, Inc, West Lafayette, Ind.) can be made from polyacrylic acid or polyacrylic acid copolymers. Superporous hydrogels of the invention include, but are not limited to, those of polyacrylamide, poly(sodium arcylate), poly(2-hydroxyethyl methacrylate), poly(hydroxypropyl methacrylate), poly(3-sulfopropyl acrylate, potassium salt), poly(2-acrylamido-2-methyl-1-propanesulfonic acid), poly({2-(acryloyloxy)ethyl}trimethyl sulfate). Poly(N-isopropyl acrylamide), poly(N-vinyl pyrrolidinone((PVP)), modified sucrose, and gelatin. Superporous hydrogels are capable of holding 50 to 200 times their weight in water (Park (2002); Dorkoosh et al. (2002)).

Compositions of the present invention, including those compositions used in methods and dressings of the invention, can also include a substantially anhydrous composition comprising a cation exchange material, such as, for example, a crosslinked, sulfonated ion exchange resin and optionally a cross-linked ionic hydrophilic polymer. In one embodiment, anhydrous compounds of the present invention comprise an alkaline earth ferrate ($M_2FeO_4$ (Fe in the +4 oxidation state), wherein M is the alkaline earth metal) and a cation exchange material. Cation exchangers contemplated within the scope of the invention include water insoluble polymers containing anionic functional groups such as $—SO_3^-$, $—OPO_3^-$, and $—COO^-$. In the practice of this invention, mixtures of insoluble polymers containing different anionic functional groups can be employed. The polymers can be cross-linked. For example, if the polymer is polystyrene, it can be cross-linked with 1% to 10% divinylbenzene. One embodiment of the present invention utilizes an ion exchange resin in the hydrogen ionic form of a sulfonated styrene divinylbenzene copolymer. Methods for preparing ion exchange resins useful in the invention are disclosed in U.S. Pat. No. 4,291,980, which was based, at least in part, on the production of spherical beads comprised of copolymer styrene and divinylbenzene as taught in U.S. Pat. Nos. 2,366,007 and 3,463,320. The counter ion in the ion-exchange resin can be any cation in the atomic table. The preferred counter-ions include hydrogen, elements in Groups IA and IIA. While the most preferred cation is hydrogen, mixed cations may be used such as hydrogen and a Group IA element and/or Group IIA element. In another embodiment, the cation-exchange material can be inorganic rather than organically based. Inorganic cation-exchange materials include, but are not limited to, natural or synthetic zeolites, hydrated alkali-aluminum silicates of the general formula $M_{2/n}O, Al_2O_3.ySiO_2.wH_2O$ where M represents a group IA or IIA element, n is the cation valence, y is 2 or greater and w is the numbe4r of water molecules contained in the channels within the zeolite. In another embodiment, ion exchange celluloses may be used where the functionalities are classified as strong acid, intermediate acid or weak acid. In another embodiment, mixtures of organic based and inorganic based ion exchangers may be used.

Compositions of the subject invention can also comprise additional optional compounds or agents that provide for increased anti-microbial, absorptive, and/or wound healing properties. In one embodiment, a composition of the invention comprises a salt ferrate, a cationic exchange resin, and a silver compound. Silver compounds include, but are not limited to, silver metal (such as nano-silver); silver halides, such as silver chlorides, silver iodides, silver bromides, silver acetate, silver benzoate, silver nitrate, silver carbonate, silver laurate, etc.; silver oxides; silver sodium hydrogen zirconium phosphate; and silver/zinc form of Zeolite A.

Additional components of compositions of the present invention can include, for example, one or more of: zinc compounds, manganese compounds, calcium compounds, and/or copper compounds or derivatives thereof. Examples include, but are not limited to, zinc oxide, zinc sulfate, zinc stearate, manganese oxide, manganese sulfate, manganese citrate, calcium oxide, calcium sulfate, calcium citrate, calcium carbonate, cuprous sulfate; alginates, carrageenans, and agars; chitosan; absorption polymers such as cross-linked polyacylates and acylate copolymers; natural and/or synthetic gums, such as guar, arabic, or karaya; oxidized celluloses; starches, such as tapioca; and drugs, such as antifungal agents and antibiotics. Antibiotics contemplated include, but are not limited to, amikacin, gentamicin, kanamycin, neomycin, netilmicin, streptomycin, tobramycin, paromomycin, geldanamycin, herbimycin, loracarbef, ertapenem, imipenem/cilastatin, meropenem, cefadroxil, cefazolin, cefalotin/cefalothin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefdinir, cefepime, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, prontosil (archaic), mafenide, sulfacetamide, sulfamethizole, sulfanilamide (archaic), sulfasalazine, sulfisoxazole, trimethoprim, trimethoprim-sulfamethoxazole (co-trimoxazole (TMP-SMX), demeclocycline, doxycycline, minocycline, oxytetracycline, tetracycline, arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin, and timidazole. Antifungal agents include, but are not limited to, natamycin, rimocidin, filipin, nystatin, amphotericin B, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, terconazole, terbinafinem amorolfine, naftifine, butenafine, andulafungin, caspofungin, micafungin, ciclopirox, flucytosine, grisefulvin, gentian violet, haloprogin, tolnaftate, and undecylenic acid.

Alkaline earth ferrate compounds and compositions of the invention can be provided in any suitable form. In one embodiment, an alkaline earth ferrate compound or composition of the invention is in a loose, free-flowing powder form. In another embodiment, an alkaline earth ferrate compound or composition of the invention is provided in a solid wafer or tablet form. Wafers, tablets, and the like can be prepared using standard methods and materials known in the art. In one embodiment, a wafer or tablet is prepared by compressing a powder composition of the invention under substantial pressure, e.g., 1,000 to 50,000 lbs/in$^2$. In one embodiment, a wafer or tablet of the invention comprises a binder, such as Carbopol 974 NF. The use of suitable binders allows wafers and tablets to be prepared at lower pressures. The wafer or tablet can be applied directly to a wound or treatment site or the wafer or tablet can be broken up or crushed into smaller pieces or powder for application to a site. Wafers and tablets can be provided in bulk form or they can be individually packaged. Alkaline earth ferrate compounds and compositions of the invention are preferably stored under substantially anhydrous conditions and preferably applied as a dry dressing.

The subject invention also concerns methods of using an alkaline earth ferrate compound or composition of the invention to stop blood flow from an open wound or surgical or medical treatment site. In one embodiment, an alkaline earth ferrate compound or composition of the invention in dry powder form is applied directly to a wound from which blood or other bodily fluids are flowing. In one embodiment, a wound or treatment site treated with an alkaline earth ferrate compound or composition of the invention is subsequently covered with a suitable wound covering or dressing. In another embodiment, a wound covering or dressing is impregnated or coated with or contains an alkaline earth ferrate compound or composition of the invention and the covering or dressing is applied to the wound. Thus, the present invention can also be practiced in conjunction with wound coverings, dressings, and protective materials, such as bandages (such as BAND-AIDS), cotton gauze, absorptive pads, and the like. Examples of wound coverings, dressings, and protective materials contemplated for use in the subject invention include those described in U.S. Pat. Nos. 7,252, 837; 7,112,714; 7,070,584; 7,030,288; 7,005,556; 6,936,746; 6,861,067; 6,787,682; 6,500,539; 6,399,092; 6,326,410; and 6,238,691.

The subject invention also concerns wound and surgical treatment site coverings, dressings, and the like. In one embodiment, a dressing of the invention comprises a pad that contains an alkaline earth ferrate compound or composition of the invention within and/or on the surface of the pad. In a specific embodiment, the pad is composed of porous foam that is sufficiently open to allow a free flow of powder to fill the voids in the porous foam. The open voids can either be random (like a foam air conditioning filter) or organized into tunnels. The tunnels can keep compositions from mixing until needed. The tunnels can be round holes or geometric shapes. Around the perimeter of the randomly open foam a less porous border may be used to contain the composition. The pad can be designed so that lateral pressure can compress the foam or tunnels and hold the composition in place for inverted application. The foam can be made from polyurethane or other polymers.

In another embodiment, a dressing of the invention comprises a pad with fibers substantially perpendicularly oriented to the plane of the pad, wherein the fibers can hold and release a composition of the present invention. The dressing can be provided with or without an integrated foam or fabric or substrate backing. The dressing can be pre-loaded with an alkaline earth ferrate compound or composition of the present invention. The dressing can be of a design wherein the fibers remain attached to the dressing during and/or after application to a wound or surgical site.

In one embodiment, a wound dressing of the invention comprises a flocked pad wherein the pad has a foam (e.g., polyurethane) portion and a flocked fibers portion. Flocking is a process of applying very short fibers onto a surface. In one embodiment, the foam portion is a porous foam as described above. In this embodiment, an alkaline earth ferrate compound or composition of the invention can be loaded onto the side of the foam opposite that of the fibers and the alkaline earth ferrate compound or composition can travel or flow through the foam and onto the fibers. The fibers can be attached to the foam portion and can be made, for example, out of calcium alginate. The fibers can be a woven or nonwoven material. The fibers can be composed of any suitable material such as cotton, wool, etc. In one embodiment, the fibers are composed of a velvet fabric. The fibers can be coated or flocked with an alkaline earth ferrate compound or composition of the present invention. Optionally, the fibers can be composed of dissolvable material (e.g., polyvinyl alcohol) or a biodegradable material (e.g., starch, calcium alginate, polysaccharides, etc.). In one embodiment, the fibers can be composed of a material that can dissolve in a solution, such as a saline solution. In another embodiment, the fibers themselves do not dissolve in solution but are attached to the pad portion via a substance or material that itself can dissolve in solution. This permits a solution to be contacted with a dressing of the invention that has been applied to a site where blood has coagulated and formed a scab, wherein the fibers dissolve or the attachment dissolves and the pad portion of the dressing can then be easily removed without ripping the scab off the wound.

In another embodiment, a dressing of the invention comprises an "island" dressing wherein the dressing has a hollow or open center area that is positioned over the wound or medical treatment site and wherein an alkaline earth ferrate compound or composition of the invention can be applied once the dressing is applied to the wound or treatment site. Alternatively, the dressing can have an alkaline earth ferrate compound or composition of the invention pre-loaded into the center of the dressing prior to application to a wound or treatment site, wherein the composition is held in place in the dressing by a suitable material that can be removed prior to use of the dressing or that can dissolve in solution or upon contact with blood at the wound or treatment site. The island dressing can be of any suitable size, and shape, and thickness appropriate for the wound site or medical procedure being performed. Preferably, the hollow center portion of the dressing where the alkaline earth ferrate compound or composition of the invention is to be applied is larger in diameter and/or circumference than the wound site or procedural site being treated. The dressing can be circular, oval, square, rectangular, diamond, trapezoid, triangular, or any other shape, including irregular shapes. The dressing can be composed of any suitable material including, but not limited to, foam, cork, plastic, woven fiber, compressed cotton, and paper materials.

In another embodiment, a dressing of the invention comprises a pouch or other container that contains an alkaline earth ferrate compound or composition of the invention and wherein at least one surface of the pouch or container that contacts the wound or treatment site is dissolvable or biodegradable in blood, bodily fluids, exudates, or other liquids or solvents. In one embodiment, a pouch can be composed of paper or paper blends, polypropylene, or polyvinyl alcohol.

In a further embodiment, an alkaline earth ferrate compound or composition of the invention is provided in a paste formulation. Carriers that can be used in a paste of the invention include long chain hydrocarbons that impart body, such as, for example, mineral oil and petroleum jelly.

The subject invention also concerns kits comprising in one or more containers or packages an alkaline earth ferrate compound or composition of the present invention. In a specific embodiment, a kit comprises an alkaline earth ferrate compound or composition comprising a sodium salt of cross-linked polyacrylate. Kits can also comprise one or more different salt ferrates of the invention, and/or a cationic exchange resin, and/or silver compound as described herein. In addition to the foregoing, kits of the invention can also include additional components, including for example, one or more of: zinc compounds, manganese compounds, calcium compounds, and/or copper compounds or derivatives thereof. Examples include, but are not limited to, zinc oxide, zinc sulfate, zinc stearate, manganese oxide, manganese sulfate, manganese citrate, calcium oxide, calcium sulfate, calcium citrate, calcium carbonate, cuprous sulfate; alginates, carrageenans, and agars; chitosan; absorption polymers such as cross-linked polyacylates and acylate copolymers; natural and/or synthetic gums, such as guar, arabic, or karaya; oxidized celluloses; starches, such as tapioca; and drugs, such as antibiotics. In one embodiment, an alkaline earth ferrate compound or composition of the invention is packaged in a container that is designed in a manner so as to preserve the anhydrous nature of the composition until the container is opened. A kit of the present invention can also comprise a wound covering, dressing, or other wound or surgical site protective material, preferably provided and maintained in sterile form until the package or container is opened for use.

The methods and compositions of the present invention can be used in the treatment of humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

The dosage or amount of an alkaline earth ferrate composition of the invention to be typically administered or applied to a site can be readily determined by an ordinarily skilled clinician and will be dependent on various factors, such as the size and type of wound or the surgical or medical procedure being performed, the amount of blood or fluid present in the wound or treatment site, and physical characteristics of the patient, as well as other drugs or treatments the patient is receiving.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Two grams of magnetite ($Fe_3O_4$) and 5 grams strontium peroxide ($SrO_2$) are intimately mixed and heated to 500° C. for 3 hours (Sr:Fe molar ratio is 1.6:1). The resulting powder is a mixture of strontium ferrate ($Sr_2FeO_4$), strontium hydroxide ($Sr(OH)_2$), and magnetite ($Fe_3O_4$). This product is an excellent hemostat with superior blood absorption, speed of solidification (~15 sec), and minimizes any stinging sensation on a wound surface. A hydrogen donor agent could be added to reduce any nominal hydroxide sting.

EXAMPLE 2

Two grams hematite ($Fe_2O_3$) is intimately mixed with 5 grams strontium peroxide ($SrO_2$) and heated to 500° C. for 3 hours (Sr:Fe molar ratio is 1.67:1). The resulting powder is a mixture of strontium ferrate ($Sr_2FeO_4$), strontium hydroxide ($Sr(OH)_2$), and hematite ($Fe_2O_3$). This too, is an excellent hemostat, with all the properties of the composition of Example 1.

The same results as above are achieved with barium peroxide as a reactant (assuming appropriate weight adjustments to match molar ratios). These reactions have not been duplicated with appropriate amounts of calcium peroxide (or magnesium peroxide) as reactants. Indeed, it is very surprising that the strontium and barium products show such a high level of hemostasis when considering their extremely poor solubility in water.

As the reaction variables are changed, the strength of the clot and the time of hardening changes to some extent. Hemostasis is achieved with product synthesized from 400° C. to 700° C., heating time from 1 to 8 hours, and molar ratios of Sr:Fe between 2:1 to 3:1. However, adverse effects may occur upon varying from the described best examples which include a soft clot, a friable clot, slow clotting time, and stinging on a real wound.

EXAMPLE 3

One gram $Ag_2O$ is mixed with 3.0 grams $SrO_2$ (molar ratio of Sr:Ag is 2.9:1) and heated to 500° C. for 3 hours. The resulting reaction product is an excellent hemostat. The $Ag_2O$ is oxidized to white AgO and the clotting time is less than 30 seconds (it should be mentioned here that this product is the only pure white hemostatic powder seen so far with excellent clotting characteristics). It is well absorbed by blood, the clot hardens quickly (<30 sec), has good adherence, and has long term anti-microbial qualities. Similar results are achieved from the reaction product produced when 1.0 gram $Ag_2O$, 3.0 grams $SrO_2$, and 0.3 grams of carbon are intimately mixed and ignited in a stainless steel crucible. This product, however, is light gray in color.

EXAMPLE 4

Bismuth oxide ($Bi_2O_3$), when reacted in the furnace with $SrO_2$ at 500° C. for 3 hours, yields a poor hemostat. However, when 1.0 gram $Bi_2O_3$, 3.0 grams $SrO_2$ and 0.3 grams of carbon are intimately mixed and ignited, an excellent hemostat is produced with a very fast clotting time (<30 seconds). More than likely, Bi (+3) is oxidized to Bi (+4) and/or Bi (+5) oxide(s).

EXAMPLE 5

The ability of strontium ferrate to stop bleeding and to form a strong seal was evaluated in mixtures with a sodium salt of cross-linked poly(acrylate). The sodium polyacrylate is a super-absorbent polymer (SAP) called "AP 80HS" from DeGussa, Germany. The strontium ferrate coded "199S" was prepared at a 3.2:1 molar ratio of Sr:Fe. Five grams of $Fe_3O_4$ and 25 grams of $SrO_2$ were mixed thoroughly and placed in a stainless steel cup and heated for 3 hours at 500° C. The $Sr_2FeO_4$ product was crushed, pulverized and screened before mixing with 80HS powder. The five mixtures at 100%, 90%, 80%, 70%, 50% and 30% 199S were evaluated in our laboratory test called the scab adhesion test. 0.1 cc of NaEDTA stabilized bovine blood from Lampire Biological Laboratories (Pipersville, Pa.) was pipetted into a small plastic boat. The blood was spread out evenly to form a one square inch wet film. 300 mg of the powder mix was poured unto the blood and left standing for 90 seconds. Excess powder was poured out leaving behind a seal formed by the powder and blood. The flat surface (5 mm) of a small stainless steel spatula was used to scrap off the weak portions of the seal. The weight of the remaining portions of the seal was weighed and recorded. During this test, visual observations can be made on blood absorption, blood coagulation, the strength and adhesion of the seal and the qualitative coverage of the remaining portions of the seal. In the absence of the super-absorbent polymer, 199S absorbed and coagulated blood very fast. However it formed a very brittle seal which gave poor strength and adhesion. Only 13 mg seal remained (see Tables 1-2).

TABLE 1

Hemostatic properties of mixtures of strontium ferrate and SAP

|  | | JH22807-8 | JH22807-9 |
|---|---|---|---|
|  | | Ratio of 80HSSAP to 199S | |
|  | 100% 199S | 1/9 80HS SAP/ 199S | 2/8 80HSSAP/ 199S |
| scab adh 1 | 13 | 67 | 167 |
| scab adh 2 |  | 63 | 191 |
| comments | very brittle excellent absorption excellent coagulation poor adhesion poor strength | brittle excellent absorption excellent coagulation weak adhesion weak strength | not brittle excellent absorption excellent coagulation excellent adhesion excellent strength |

TABLE 2

Hemostatic properties of mixtures of strontium ferrate and SAP

|  | JH22807-10 | JH22807-11 | JH32807-42 |
|---|---|---|---|
|  | Ratio of 80HSSAP to 199S | | |
|  | 3/7 80HSSAP/ 199S | 1/1 80HSSAP/ 199S | 7/3 80HSSAP/ 199S |
| scab adh 1 (mg) | 176 | 208 | 55 |
| scab adh 2 (mg) | 202 | 131 | 46 |
| comments | more flexible excellent | very flexible excellent | too flexible excellent |

TABLE 2-continued

Hemostatic properties of mixtures of strontium ferrate and SAP

|  | JH22807-10 | JH22807-11 | JH32807-42 |
|---|---|---|---|
|  | Ratio of 80HSSAP to 199S | | |
|  | 3/7 80HSSAP/ 199S | 1/1 80HSSAP/ 199S | 7/3 80HSSAP/ 199S |
|  | absorption excellent coagulation excellent adhesion excellent strength | absorption excellent coagulation excellent adhesion excellent strength | absorption very good coagulation fair adhesion good strength |

The addition of 10% SAP to $Sr_2FeO_4$ gave a less brittle seal with somewhat improved adhesion and strength without scarifying absorption and coagulation. The amount of seal left after scrapping was 65 mg (mean of two tests). The seal became more flexible with increasing addition of SAP (20%, 30%, and 50%) while absorption, coagulation, adhesion and strength were excellent. The amount of seal left after scrapping ranged from 131 mg to mg. However, properties start to fall off at 70% SAP, adhesion worsens and the seal remaining after scrapping is reduced significantly.

EXAMPLE 6

The seal formed by $Sr_2FeO_4$ is affected by the type of super-absorbent polymer (SAP) used. AP-80HS is a finer version of CABLOC 3050, also available from DeGussa, Germany. When evaluated at 30% addition of SAP to $Sr_2FeO_4$, the strength and adhesion of the seal formed with porcine blood is better for the finer version. The amount of coverage remaining after the seal is scrapped is also greater for the mixture with the finer SAP.

EXAMPLE 7

Strontium ferrate is very insoluble in water or in saline solution. The small amount of strontium ferrate that is soluble reacts with water to form strontium hydroxide and ferric oxide. Ferric oxide is insoluble in water while strontium hydroxide is slightly soluble in water, 1 part in 50 parts of water. The hydroxide can be neutralized with any acid donors. In this example, we investigated how the hydrogen form of cross-linked poly(styrene)sulfonic acid ion-exchange resin (described as H resin) would influence the hemostatic properties of mixtures of strontium ferrate and SAP. Five compositions (designated as JH32907-43, JH32907-44, JH32907-45, JH32907-46, and JH32907-47) containing decreasing of H resin were prepared as described in Table 3 (percentage of each material is shown). The strontium ferrate used was coded "207S". 207S has the same starting raw material composition as strontium ferrate coded "199S". The properties of the seal formed between these compositions are also summarized in the table. Compositions containing higher amounts (41.5% and 33%) of H resin provided weak seals. Lowering the amounts of H resin provided increasingly better seals. At 10% H resin, the seal remaining after scrapping was excellent.

TABLE 3

Effects of mixing an acidic ion exchange resin on the seal formed by $Sr_2FeO_4$ and SAP with bovine blood.

|  | JH32907-43 | JH32907-44 | JH32907-45 | JH32907-46 | JH32907-47 |
|---|---|---|---|---|---|
| $SrFeO_4$ - 207S* | 41.5% | 50% | 60% | 68% | 73% |
| 80HS SAP* | 17% | 17% | 17% | 16.5% | 17% |
| H resin (125 um)* | 41.5% | 33% | 23% | 15.5% | 10% |

TABLE 3-continued

Effects of mixing an acidic ion exchange resin on the seal formed by $Sr_2FeO_4$ and SAP with bovine blood.

|  | JH32907-43 | JH32907-44 | JH32907-45 | JH32907-46 | JH32907-47 |
|---|---|---|---|---|---|
| scab adh 1 (mg) | 10 | 29 | 48 | 89 | 124 |
| scab adh 2 (mg) | 20 | 26 | 62 | 95 | 93 |
| blood absorption | weak | fair | good | very good | excellent |
| blood coagulation | weak | fair | good | very good | excellent |
| strength | poor | weak | good | very good | excellent |
| adhesion | poor | weak | good | very good | excellent |
| % coverage | 15 | 25 | 60 | 65-70 | 75-90 |

*shown as a percentage of each material

EXAMPLE 7

Figure 1:
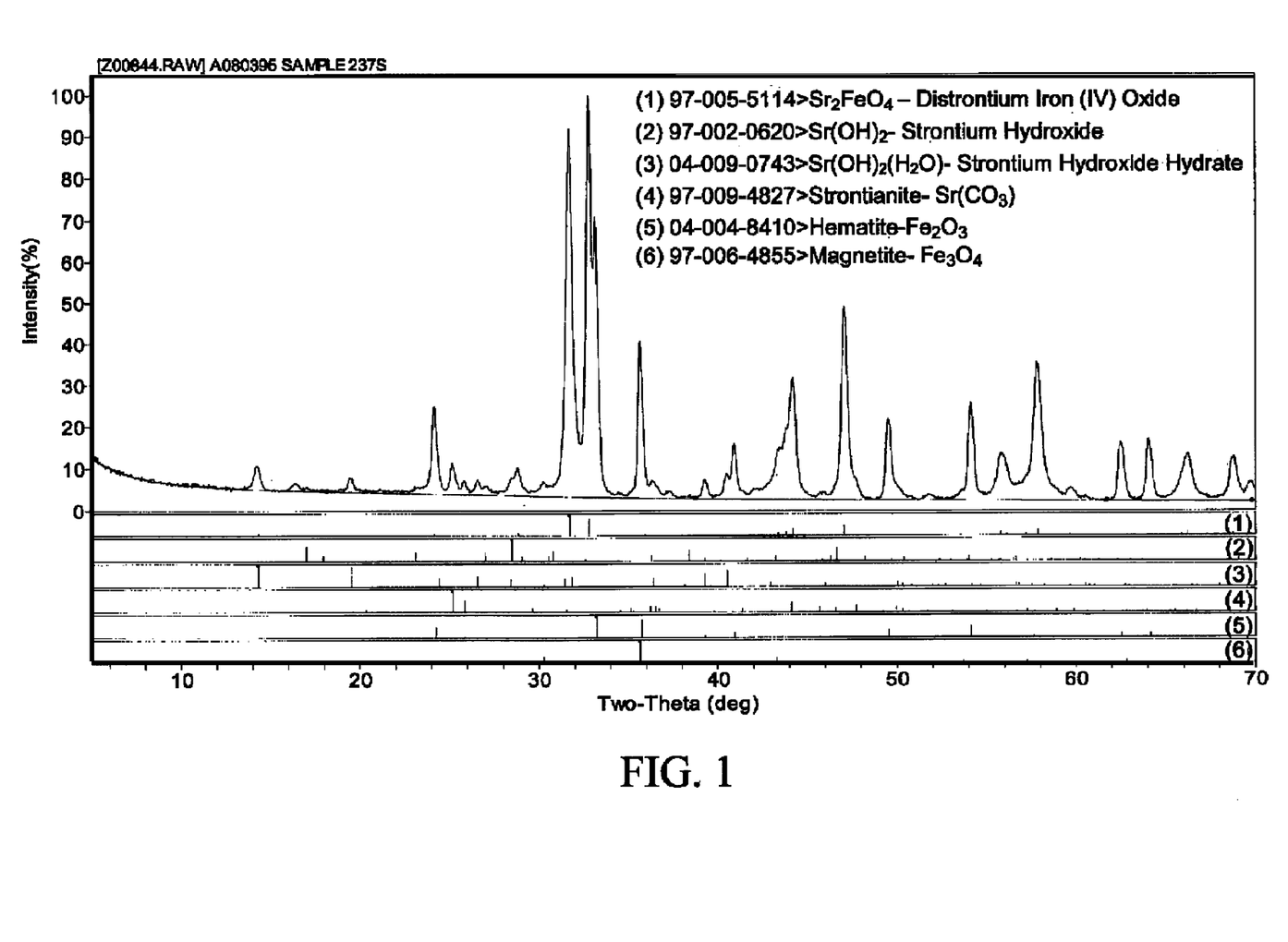
FIG. 1 shows X-Ray Diffraction Analyses of $Sr_2FeO_4$ (Sr oxidation state is +2) sample 237S.
Figure 2:
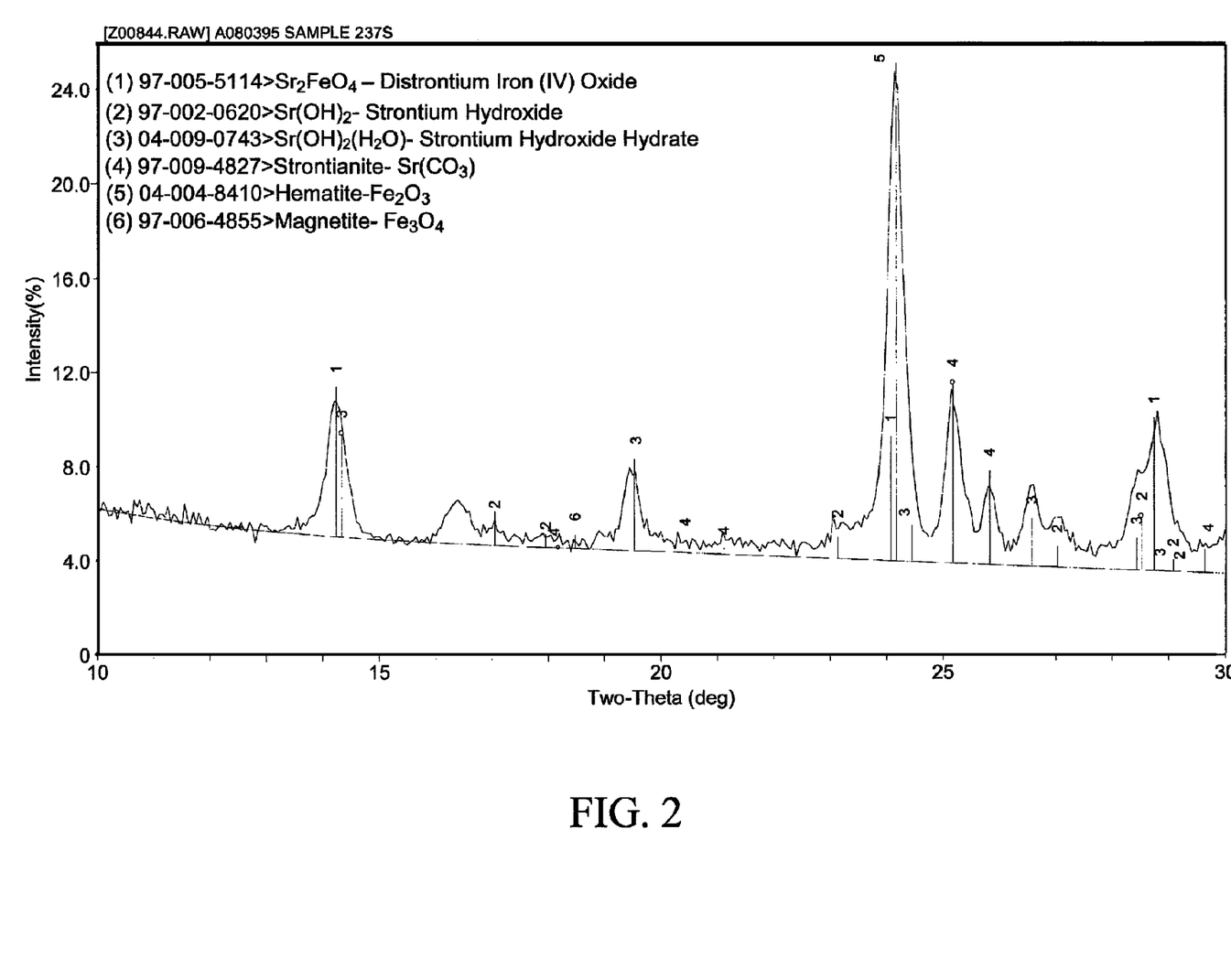
FIGS. 2-4 are expanded portions of the graph shown in FIG. 1.
Figure 3:
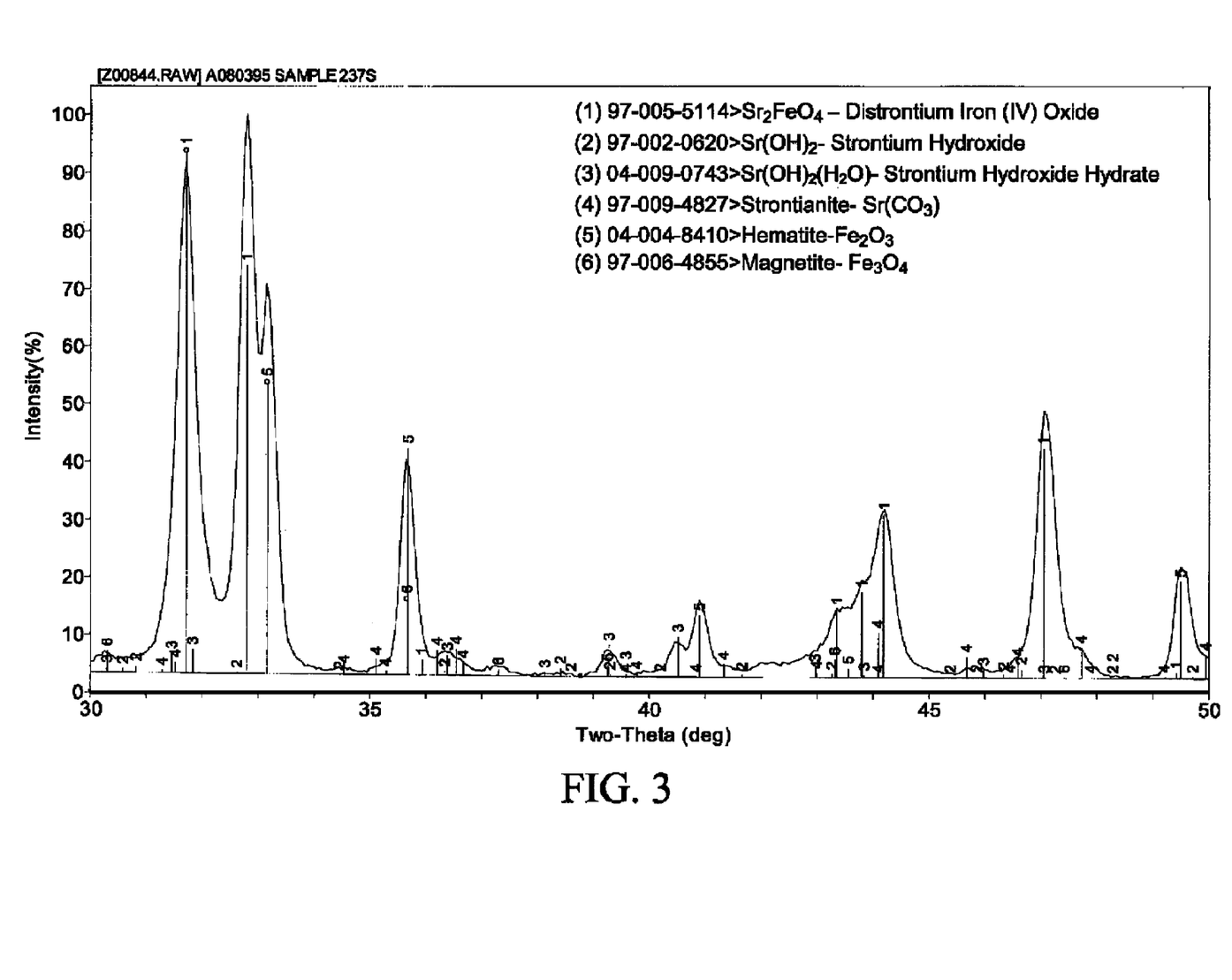
Figure 4:
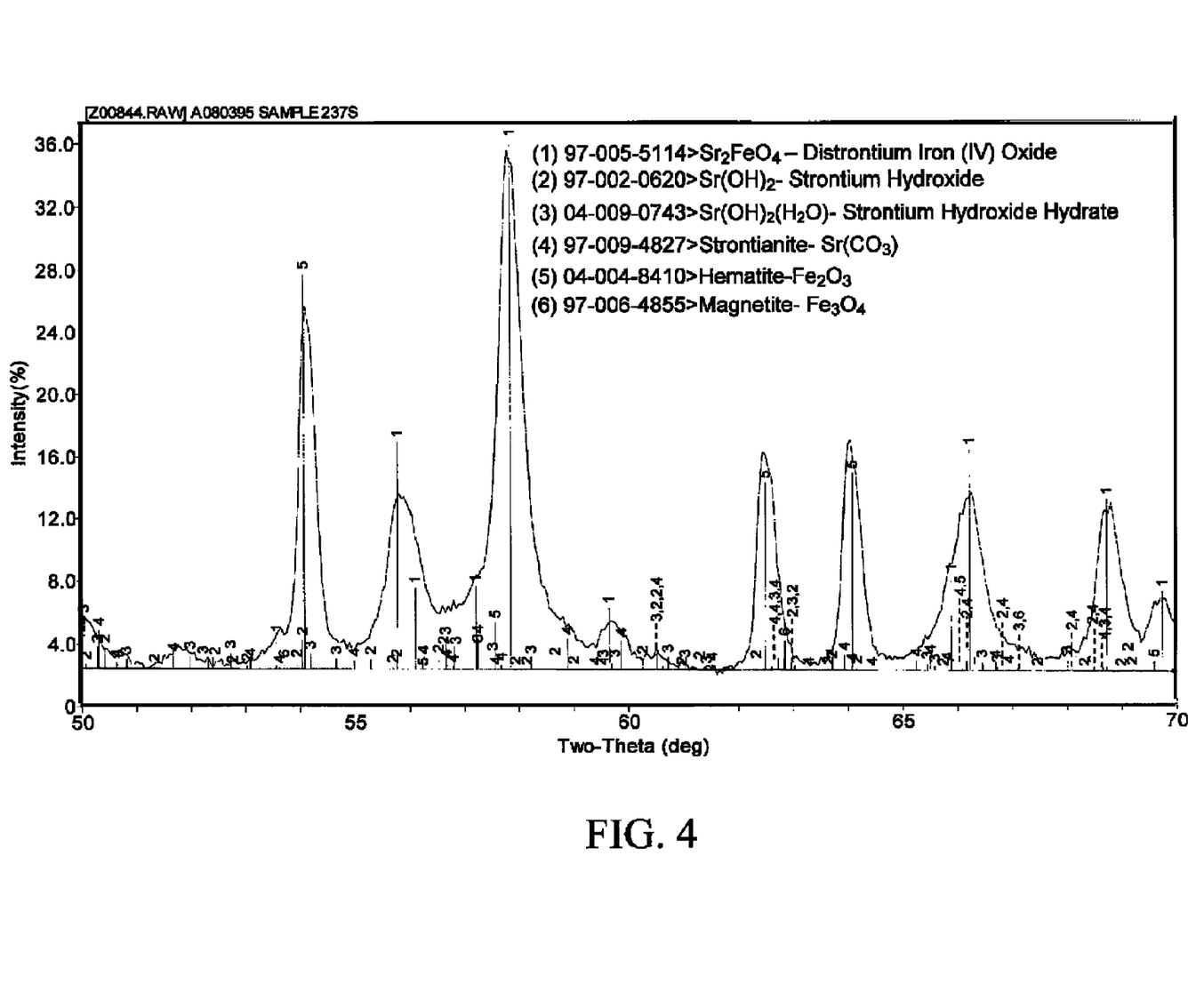
Figure 5:
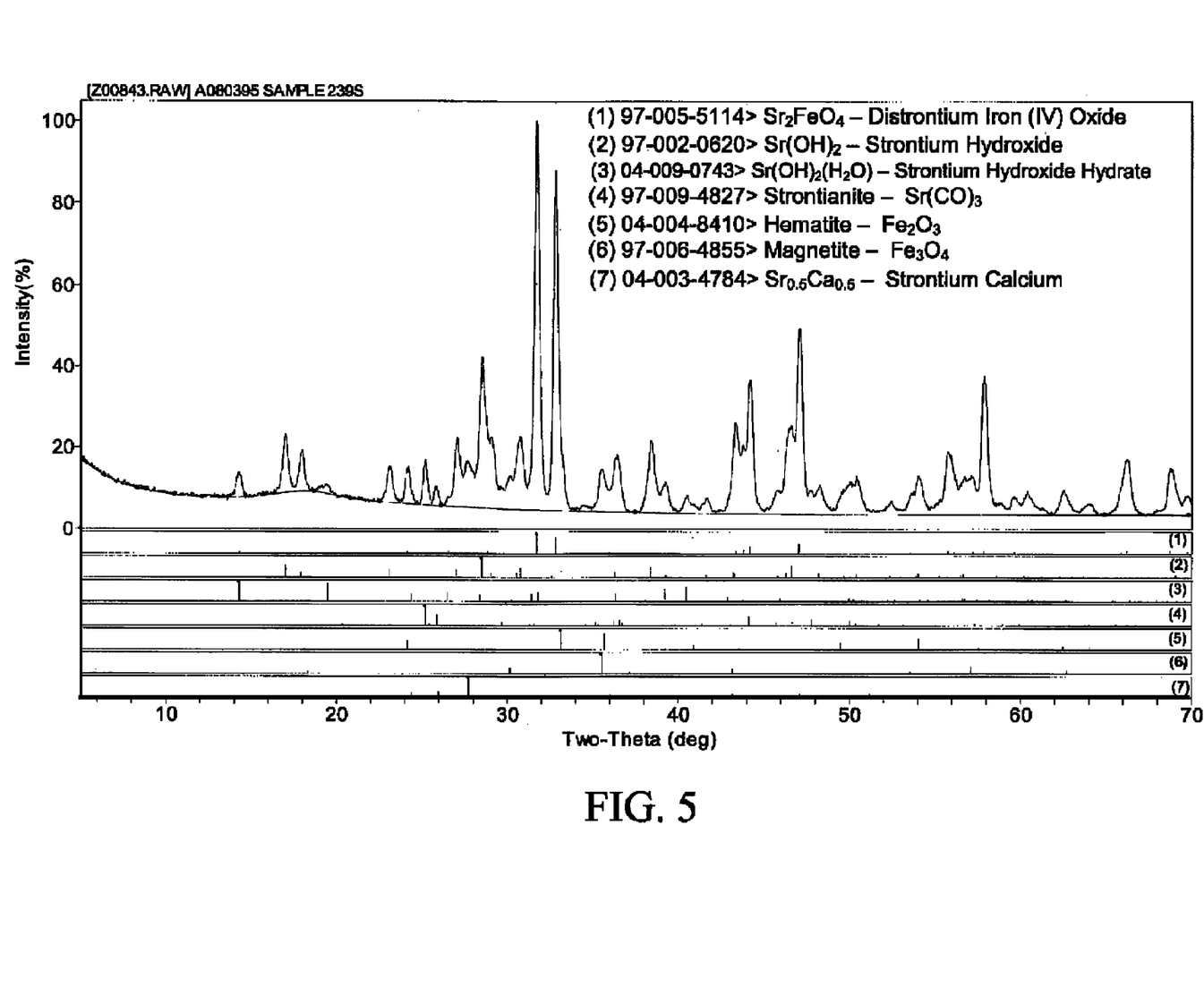
FIG. 5 shows X-Ray Diffraction Analyses of $Sr_2FeO_4$ (Sr oxidation state is +2) sample 239S.
Figure 6:
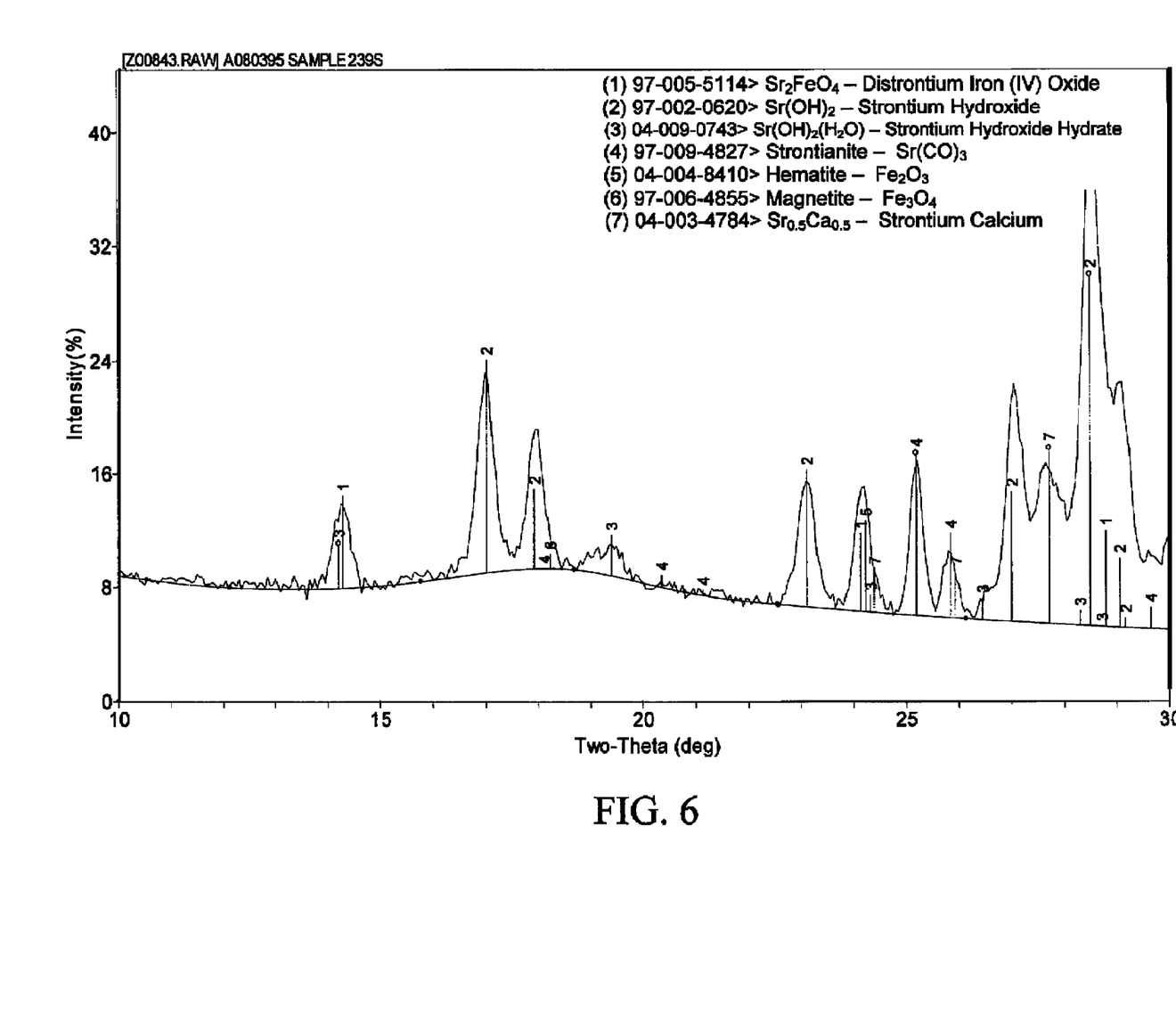
FIGS. 6-8 are expanded portions of the graph shown in FIG. 5.
Figure 7:
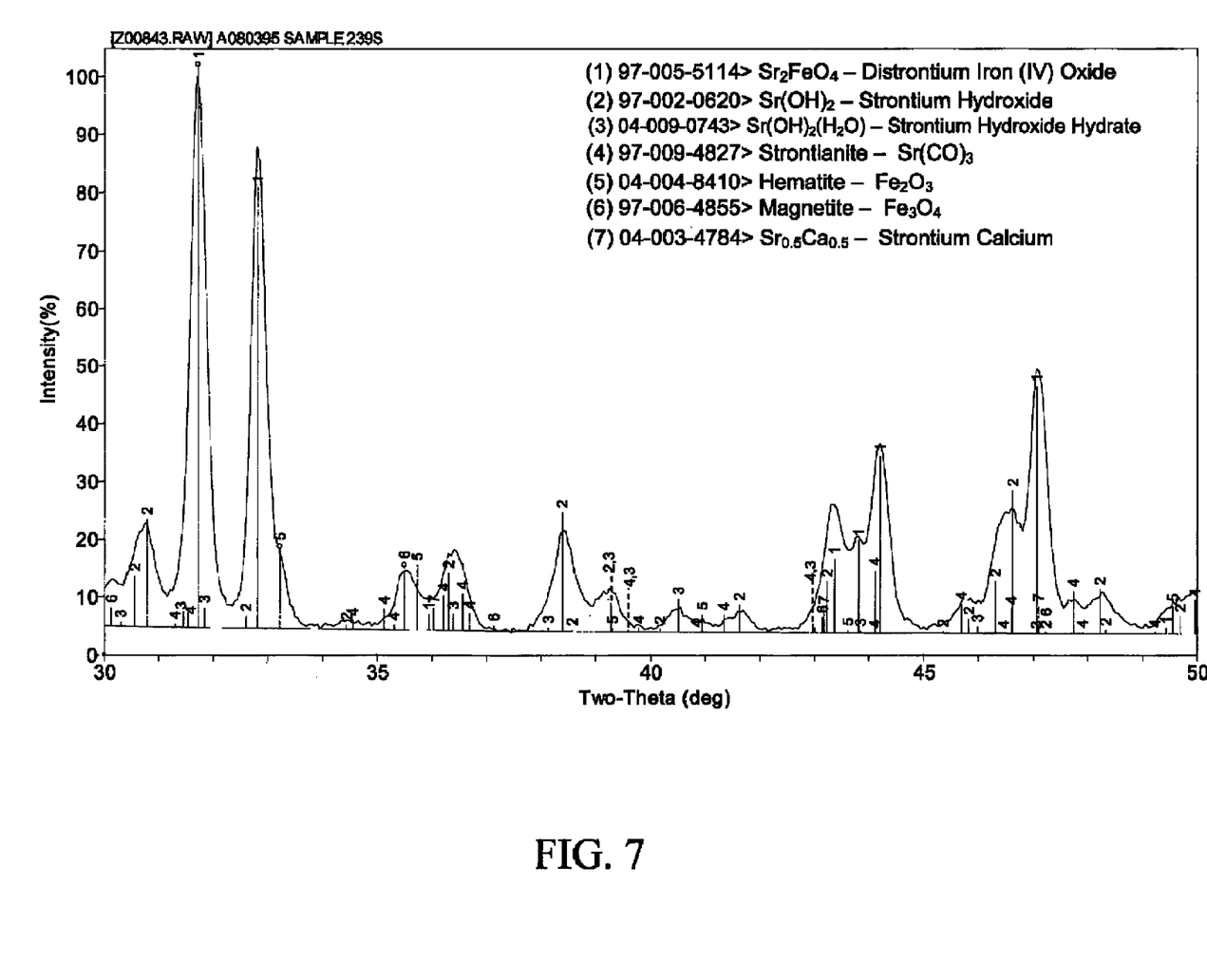
Figure 8:
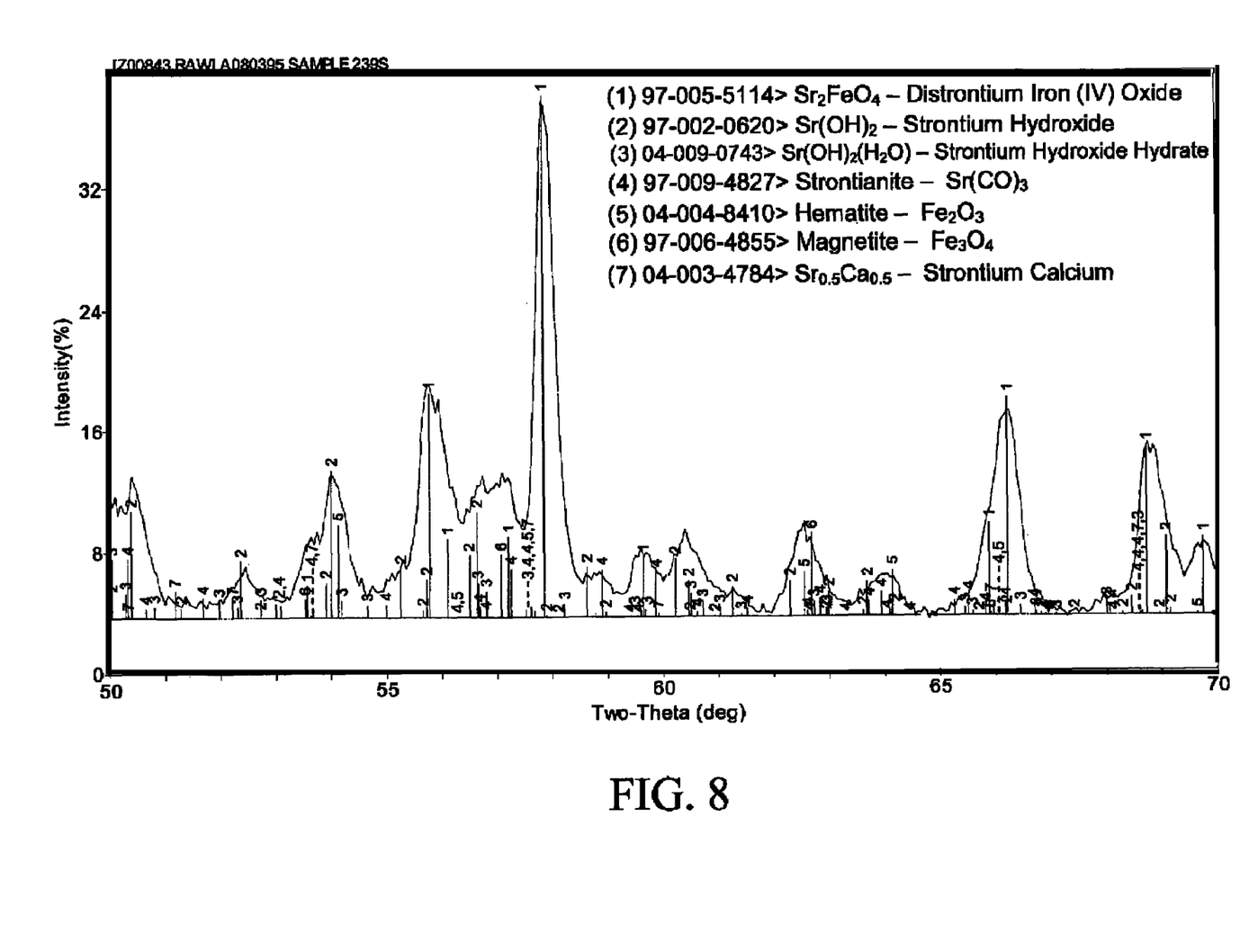

X-Ray Diffraction Analyses of compositions of $Sr_2FeO_4$ produced according to the subject invention are shown in FIGS. 1-8. The samples are coded as "237S" and "239S". The strontium in $Sr_2FeO_4$ has a +2 oxidation state. Table 4 shows compositional analysis of samples 237S and 239S.

TABLE 4

|  | Quantitative Analysis (wt %) | |
|---|---|---|
|  | 237S | 239S |
| $Sr_2FeO_4$ | 53.9 ± 1.1% | 48.9 ± 1.0% |
| $Sr(OH)_2$ | 2.1 ± 0.4% | 29.2 ± 0.7% |
| $Sr(OH)_2 \cdot H_2O$ | 2.8 ± 0.3% | 3.4 ± 0.3% |
| $SrCO_3$ | 3.3 ± 0.3% | 6.3 ± 0.3% |
| $Fe_2O_3$ (Hematite) | 38.0 ± 0.9% | 4.7 ± 0.5% |
| $Fe_3O_4$ (Magnetite) |  | 4.2 ± 0.3% |
| (Sr, Ca) - tentative |  | 3.3 ± 0.2% |

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 2,366,007
U.S. Pat. No. 3,463,320
U.S. Pat. No. 3,669,103
U.S. Pat. No. 3,670,731
U.S. Pat. No. 4,291,980
U.S. Pat. No. 4,545,974
U.S. Pat. No. 4,654,039
U.S. Pat. No. 5,461,085
U.S. Pat. No. 5,525,703
U.S. Pat. No. 5,612,384
U.S. Pat. No. 6,187,347
U.S. Pat. No. 6,238,691
U.S. Pat. No. 6,271,278
U.S. Pat. No. 6,326,410
U.S. Pat. No. 6,399,092
U.S. Pat. No. 6,500,539
U.S. Pat. No. 6,521,265
U.S. Pat. No. 6,787,682
U.S. Pat. No. 6,861,067
U.S. Pat. No. 6,936,746
U.S. Pat. No. 6,960,617
U.S. Pat. No. 7,005,556
U.S. Pat. No. 7,030,288
U.S. Pat. No. 7,056,957
U.S. Pat. No. 7,070,584
U.S. Pat. No. 7,112,714
U.S. Pat. No. 7,252,837
U.S. Published Application No. 2001/0038831
U.S. Published Application No. 2002/0141964
U.S. Published Application No. 2003/0008007
U.S. Published Application No. 2003/02332895
U.S. Published Application No. 2004/022402
U.S. Published Application No. 2007/0269499
EP 0312952
EP 0441507
Sidgwick, N. V. "The Chemical Elements And Their Compounds" Oxford University Press; 1950; p. 1420.
Vol'nov, I. I. "Peroxides, Superoxides, and Ozonides of Alkali and Alkaline Earth Metals;" Plenum Press; New York; 1966.
Dorkoosh F. A. et al., (2002), "Evaluation of superporous hydrogel and composite in porcine intestine ex-vivo", *Eur J Pharm Biopharm*, 53: 161-166.
Park, K., July/August (2002), "Superporous Hydrogels for Pharmaceutical & Other Applications", *Drug Delivery Technologies*, Vol. 2, No. 5.

We claim:

1. A method for preparing an alkaline earth ferrate of formula $M_2FeO_4$ wherein M is an alkaline earth metal, said method comprising heat treating an alkaline earth oxide and/or peroxide intimately mixed with an iron oxide at a temperature between about 400° C. and 700° C. for between about 15 minutes to about 15 hours, wherein the yield of said alkaline earth ferrate is greater than about 48% (weight %).

2. The method according to claim 1, wherein said alkaline earth peroxide is $SrO_2$.

3. The method according to claim 1, wherein said iron oxide is $Fe_3O_4$ or $Fe_2O_3$.

4. The method according to claim 1, wherein the molar ratio of the alkaline earth oxide or alkaline earth peroxide to Fe in the mixture is from about 5:1 to about 1:5.

5. The method according to claim 1, wherein said method comprises isolating said alkaline earth ferrate from said heat treated mixture.

6. The method according to claim 1, wherein M is Sr.

7. The method according to claim 1, wherein said alkaline earth ferrate is $Sr_2FeO_4$.

8. The method according to claim 1, wherein said heat treatment comprises heating for about 1 hour.

9. The method according to claim 1, wherein said heat treatment comprises heating for about 7 hours.

10. The method according to claim 1, wherein said heat treatment comprises heating at about 400° C.

11. The method according to claim 1, wherein said heat treatment comprises heating at about 500° C.

12. The method according to claim 1, wherein said heat treatment comprises heating at about 600° C.

13. The method according to claim 1, wherein said heat treatment comprises heating at about 700° C. for between about 15 minutes to about 30 minutes.

14. The method according to claim 10, wherein said heat treatment comprises heating for about 15 hours.

15. The method according to claim 11, wherein said heat treatment comprises heating for about 3 hours.

16. The method according to claim 12, wherein said heat treatment comprises heating for about 30 minutes.

17. The method according to claim 13, wherein said heat treatment comprises heating for between about 15 minutes to about 30 minutes.

18. The method according to claim 1, wherein said alkaline earth peroxide is $SrO_2$ and said iron oxide is $Fe_3O_4$ or $Fe_2O_3$.

19. The method according to claim 1, wherein the yield of said alkaline earth ferrate is greater than about 53% (weight %).

* * * * *

UNITED STATES PATENT AND TRADEMARK OFFICE
CERTIFICATE OF CORRECTION

PATENT NO. : 8,372,441 B2
APPLICATION NO. : 12/627900
DATED : February 12, 2013
INVENTOR(S) : John Alfred Thompson and John Hen Page 1 of 1

It is certified that error appears in the above-identified patent and that said Letters Patent is hereby corrected as shown below:

In the Claims:

Column 6,
Line 61, "and timidazole" should read --and tinidazole--.

Column 12,
Line 21, "131 mg to mg" should read --131 mg to 208 mg--.

Signed and Sealed this
Twenty-third Day of July, 2013

Teresa Stanek Rea
*Acting Director of the United States Patent and Trademark Office*